United States Patent
Xu et al.

(10) Patent No.: US 6,946,452 B2
(45) Date of Patent: Sep. 20, 2005

(54) USE OF N-ACETYL-D-GLUCOSAMINE IN THE MANUFACTURE OF PHARMACEUTICAL USEFUL FOR TREATING MOTION SICKNESS

(75) Inventors: Qiwang Xu, Chongoing (CN); Junkang Liu, Chongoing (CN); Zetao Yuan, Chongoing (CN)

(73) Assignees: Third Military Medical University Chinese People's Liberation Army P.R. of China, Chongqing (CN); Bio-Wave Institute of Suzhou Hi-Teach New District Corporation, LTD, Jiangsu (CN); Beijing Sino-Hongkong Dafu Science & Technology of Biowave Co., Ltd., Beijing (CN)

( * ) Notice: Subject to any disclaimer, the term of this patent is extended or adjusted under 35 U.S.C. 154(b) by 0 days.

(21) Appl. No.: 10/469,326
(22) PCT Filed: Feb. 28, 2002
(86) PCT No.: PCT/CN02/00117
§ 371 (c)(1), (2), (4) Date: Feb. 3, 2004
(87) PCT Pub. No.: WO02/067944
PCT Pub. Date: Sep. 6, 2002

(65) Prior Publication Data
US 2004/0116383 A1 Jun. 17, 2004

(30) Foreign Application Priority Data
Feb. 28, 2001 (CN) .............................. 1104892

(51) Int. Cl.$^7$ ......................... A01N 43/04; A61K 31/70
(52) U.S. Cl. ....................................... 514/62; 536/55.2
(58) Field of Search ........................... 514/62; 536/55.2

(56) References Cited

U.S. PATENT DOCUMENTS 4,777,170 A * 10/1988 Heinrich ................... 514/226.2
6,140,324 A * 10/2000 Tattersall ................. 514/226.2
6,159,485 A * 12/2000 Yu et al. ..................... 424/401

FOREIGN PATENT DOCUMENTS

| CN | 1156026 | 8/1997 |
| CN | 1156027 | 8/1997 |
| CN | 1156028 | 8/1997 |
| WO | 93/14765 | 8/1993 |
| WO | 93/18775 | 9/1993 |

* cited by examiner

Primary Examiner—James O. Wilson
Assistant Examiner—Traviss C. McIntosh, III
(74) Attorney, Agent, or Firm—Ladas & Parry

(57) ABSTRACT

The present invention has disclosed a use of N-acetyl-D-glucosamine in the manufacture of a medicament for preventing and treating motion sickness, the preparation in which N-acetyl-D-glucosamine is taken as a main active component is able to be used for preventing and treating motion sickness with an effective rate up to more than 90%.

8 Claims, No Drawings

USE OF N-ACETYL-D-GLUCOSAMINE IN THE MANUFACTURE OF PHARMACEUTICAL USEFUL FOR TREATING MOTION SICKNESS

TECHNICAL FIELD

The present invention relates to the use of N-acetyl-D-glucosamine in the manufacture of a medicament for preventing and treating the motion sickness.

BACKGROUND ART

Motion sickness is a general denomination of carsickness, seasickness, airsickness and a disease caused by swinging, bumping, rotation, accelerated moving and other various factors. The disease often appears several minutes or hours after riding, navigating, flying and other movements. The patient firstly feels uncomfortable in the upper stomach, then nauseated, looks pale, breaks into a cold sweat; after that, dizziness, mental depression, secreted sputum increase and vomiting may occur, and there may be a blood-pressure decrease, irregular breathing, nystagmus. Serious vomiting may cause deprivation of body fluids and a disorder of electrolytes. Generally, the symptom will disappear or lighten several ten minutes or several hours after stopping the motion or decelerating the velocity. There is also a possibility that the patient can not recover even several days later, and be dispirited, and have limb asthenia. When the motions or accelerations are repeated, the symptoms may reappear.

The disease is mainly related to the function of vestibule. The cysto-ciliary cell of oval vesicle and sphere vesicle of internal ear labyrinth in the vestibule can mainly feel the linear motion up and down, right and left. The ampullary crest ciliary cell of three semicircular canals mainly feel the rotation motion. There are many static cilia and one dynamic cilium in each ciliary cell, the cilia are covered with colloidal membrane consisting of glycoprotein, mucopolysaccharide. The colloidal membrane (anpullae cap, statolithic membrane) can interact with cilia to form a location sensor. When starting or stopping the rotation or linear motion, the displacement of inner lymph will lead to the displacement of the colloid membrane, so applying stimulation to the cilia, and the excitation caused by ciliary cell is passed into cerebra through the vestibular nerve. The ciliary swing of normal person's ciliary cell is in a chaos rhythm, which is very easy to couple and adapt with a random stimulation caused by outside motion. But the ciliary swing of the ciliary cell of a patient suffering from motion sickness is in a quasi-periodicity, so it is difficult to couple with the random stimulation caused by outside motion, leading to a continuous excitation of the ciliary cell, which is transferred from the vestibular nerve to the vestibular nerval nucleus, then transferred to the cerebellum and hypothalamus in proper order, causing a series of clinical symptoms. The stimulation to vestibular may affect the structure of the network, induce the reduction of blood pressure and vomiting. Vestibular nerval nucleus may cause nystagmus from the medial longitudinal fiber to eye muscle motor nuclei; after the cerebellum and hypothalamus suffer from nerval impulse, the change of the muscular tension all over the body will occur. The stimulation to cerebellum may also be another mechanism of this disease.

At present, there is not an effective way for preventing and treating motion sickness. The pending solutions mainly use anti-histamine agents and belladonna agents, or an anti-vomiting agent (metoclopramide), or sedative (such as phenobarbital). These medicaments have large side effects, and bring many inconveniences to trips and to living.

CONTENTS OF THE INVENTION

The object of the present invention is to provide a new method and medicament for preventing and treating motion sickness disease.

The applicant of the present invention has surprisingly found that N-acetyl-Dglucosamine and pharmaceutical acceptable salts thereof are able to effectively prevent and cure motion sickness disease. Because N-acetyl-Dglucosamine has no toxicity, and have a unique curative effect, without influence on the trip and living, it can be used widely for a long period.

Therefore, the present invention is related to a method for preventing and treating the motion sickness, including administering to a patient who is in need thereof of an effective amount of N-acetyl-D glucosamine and pharmaceutical acceptable salts thereof.

On the other hand, the present invention is related to the use of N-acetyl-D-glucosamine and pharmaceutical acceptable salts thereof in the manufacture of a medicament for preventing and treating motion sickness disease.

In the research of "bio-waves" theory, the present inventor has set up a bacterial wave growth model. Through research, it is known that this wave is of its intrinsic regulation mechanism: some chemical substances are able to participate in regulation in the bio-wave process, so as to transform an abnormal periodic slow wave into a normal physiological chaotic quick wave, and these kinds of substances are known as promoting wave factors. Through separating, purifying and identifying, it is determined that one of the factors is N-acetyl-D-glucosamine, the promoting wave function of which is shown in lubricating and protecting the cell. Many biochemical and physiological processes of the human body need the participation of the promoting wave factors, and it would lead to an abnormal state, if this kind of promoting wave factors is missing in the living body.

The structure of N-acetyl-D-glucosamine is as follows:

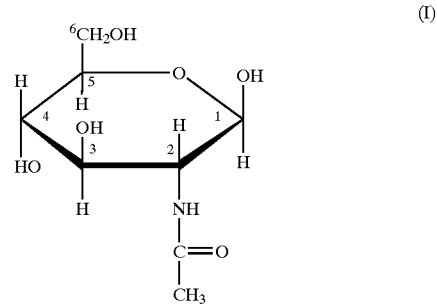

N-acetyl-D-glucosamine can be purchased in the market or prepared according to known methods. For instance, patent application WO97/31121 has disclosed a method for preparing N-acetyl-D-glucosamine from chitin by enzyme method, Japanese patent application JP63273493 has disclosed a method in which chitin is partially hydrolyzed into N-acetyl-chitose, and then it is treated with enzyme to obtain N-acetyl-D-glucosamine.

The pharmaceutical acceptable salts of N-acetyl-D-glucosamine that can be mentioned are the salts formed with pharmaceutical acceptable acids, for instance, the salts formed with inorganic acids, such as hydrochloride, hydrobromide, borate, phosphate, sulfate sulfite and hydrophosphate, and the salts formed with organic acids, such as citrate, benzoate, ascorbate, methyl sulfate, naphthalene-2-sulfonate, picrate, fumarate, maleate, malonate, oxalate, succinate, acetate, tartrate, mesylate, tosylate, isethionate, α-ketoglutarate, α-glyceryl phosphate and glucose-1-phosphate.

N-acetyl-D-glucosamine is a chemical reagent. From the 1990's, it is continually used to treat pericementitis (WO9102530A1), microbiological infection (WO9718790A3), intestinal inflammation (WO9953929A1), cornea disease (JP10287570A2), hypertrophy of the prostate (U.S. Pat. No. 5,116,615) and so on. It is also applied in cosmetology (JP59013708A2), shampoo preparation (JP2011505A2), tissue growth regulation agent (WO/A 8 702244), and etc., but it has not been used in the manufacture of a medicament for preventing and treating motion sickness.

The applicant of the present invention has found that N-acetyl-D-glucosamine is able to effectively prevent and treat motion sickness. Because its toxicity and side effects are very light, using N-acetyl-D-glucosamine to prevent and treat motion sickness may avoid undesired side effects caused by current medicaments for preventing and treating the disease. Depending upon the necessity, a small dosage for a long term treatment or a large dosage for a short term treatment can be adopted.

For the purpose of treating the motion sickness disease, N-acetyl-D-glucosamine can be used alone or used in the form of a pharmaceutical preparation made by combining with pharmaceutical acceptable excipients or/and carriers. This kind of preparation can be in any form for convenient traditional administrations. Preferably, the preparations are in the form of liquid or solid for oral administration. A conventional method can be used to prepare the medical compositions in the form of suitable pharmaceutical preparations, for instance mixing, granulating, tableting, sugar coating, film coating and so on. The liquid preparations for oral administration may use aseptic water and aseptic saline solution as carriers, and alcoholic drinks like alcohols may also be taken used as carriers. In a preferred embodiment, the concentration of N-acetyl-D-glucosamine in alcoholic drink is 0.1~4% by weight. For a solid preparation such as a tablet or capsule, in addition to the compound of formula (I), it may also include diluent, such as lactose, glucose, cellulose, starch, lubricant such as silica, talc, magnesium stearate or calcium stearate, and/or polyglycol; binder such as starch, Arabic gum, methyl cellulose, carboxymethyl cellulose, polyvinylpyrrolidone; depolymerizing agent such as starch, alginic acid, aliginate, starch sodium glycolate; foaming mixture; colorant; sweetener; lubricant such as lecithin, polyethenoxy ether and so on.

Preferably, said medicament is administrated to the patients in need thereof orally with a dosage of 1000~10000 mg of N-acetyl-D-glucosamine daily in the period from 2~3 days before the trip to the end of the trip, wherein the trip is by car, navigation or flying, for preventing and treating motion sickness disease in a short period.

In the same way, preferably, said medicament is administrated to the patients in need thereof orally with a dosage of 200~2000 mg of N-acetyl-D-glucosamine daily, for preventing and treating motion sickness disease in a long period.

More preferably, the medicament with alcoholic drink as carrier is administrated to the patient in need thereof orally with a dosage of 200~1000 mg of N-acetyl-D-glucosamine daily in the period from 2~3 days before the trip to the end of the trip, wherein the trip is by car, navigation or flying.

Though having no intention to be limited to any theory, the applicant thinks that motion sickness is substantially a disease caused by losing coupling due to oscillation. As a regulating factor of the bio-waves, N-acetyl-D-glucosamine possesses a wide regulating function to the bio-waves. Through the following three aspects, it is able to develop its special effect in preventing and treating the motion sickness:

(1) Regulating the rhythmical wave of the cilia in the internal ear ciliary cell. The swinging of ciliary cluster in the ciliary cell is in rhythm, and can be regulated. But N-acetyl-D-glucosamine is able to regulate the quasi-periodic wave of the cilia swing of the ciliary cell of the patient to form a chaos wave, so as to make it easy to couple with outside random rhythm and raise adaptive ability of the patient to the outside motion.

(2) Regulating the viscosity of ampullae cap and statolithic membrane. Ampullae cap and statolithic membrane are both colloidal membranes formed by glycoprotein as a main component, which transfer the motion of the outside world so as to produce an action to the cilia of ciliary cell, N-acetyl-D-glucosamine is a precursor substance of glycoprotein, which can promote the ciliary cell to secrete glycoprotein so as to raise the viscosity of the colloid membrane. Increasing viscosity will strengthen the coupling between colloid membrane and cilia, favorable to the coupling between the swing of cilia and outside motion.

(3) Regulating the excitation of vegetative nerve and vestibule nerve. N-acetyl-D-glucosamine is able to regulate the waves of the nerval cell and network thereof. The continuous single wave transferred from ciliary cell to vestibule nerve, cerebellum, hypothalami and vegetative nerve is regulated into a shape-separating chaos wave. After subjecting to disturbance, the movement of vegetative nerve and vagus nerve also tends to an absorbed point so as to relieve or remove nauseating, vomiting, paleness cold sweats, dizziness, decreased blood pressure, nystagmus and so on.

OPTIMAL MODE FOR CARRYING OUT THE INVENTION

The following experimental examples are used to illustrate the promoting wave function, low toxicity, and the effect for preventing and treating motion sickness disease, of N-acetyl-D-glucosamine (NAG).

I. Promoting Wave Test of N-acetyl-D-glucosamine

1. Experimental Materials and Method:

1.1 Samples: Pure Compound of Formula (I)

1.2 Experimental Materials:

Strain: Proteus Mirabilis (which should comply with the following biological reaction characteristics: dynamics (+), urease (+), lactose (−), glucose (+), $H_2S$ (−), phenylalanine deaminase (+).

Culture medium: modified LB culture medium (the components of the composition are: trytones of 1%, yeast extract of 0.5%, sodium chloride 1%, glucose of 0.1%, TTC of 0.002% and pH=7.2~7.4).

1.3 Experimental Method:

The Proteus Mirabilis were inoculated at the center of LB plate, incubating at 37° C. for 9 hours, then there were concentric rings emerged, which were extended outward continually with an interval of 3 hours, and this was taken as a control; adding the compound of formula (I) with final concentration of 0.5% onto the LB plate, The Proteus Mirabilis were innoculated by the same method, cultured at 37° C., and the result showed that not only the concentric rings formed with an interval of 3 hours were emerged, comparing with the control, it can be seen that there were also many fine waves on each ring emerged.

2. Experimental Results and Evaluation:

The experiment adopts a bio-wave model which is used to research the promoting wave function of N-acetyl-D-glucosamine. It can be seen from the results that the compound of formula (I) was not only able to cause bacterial cell to reveal a normal bio-wave characteristic, but also to cause the wave to reveal a finer wave mode, and these indicated that N-acetyl-D-glucosamine have promoting function to bio-waves, and the promoting wave function is able to participate in the coupling oscillation waving procedure conducted by inner ear ciliary cell and nerve system.

II. Toxicological Test of the Compound of Formula (I), including:

1. acute toxicity test: including tests of administrating medicine by oral, Intravenous injection and maximum limit amount for administration;
2. Ames test;
3. micronucleus test of bone marrow cell of mouse;
4. abnormal sexual test for the sperm of mouse;
5. abnormal aberrance test for the chromosin of mouse's testis;
6. chronic lethal test;
7. subchronic toxicity (feed for 90 days) test;
8. traditional aberrance-inducing test;

The results from these tests show that in the acute toxicity test of the compound of formula (I), a dosage of more than 2 g/kg is taken, which is 300 times greater than the injection dosage for human being, but the acute toxicosis reaction had not appeared yet. In the long-period toxicity test, the maximum dosage has reached up to 1 g/kg, and after the treatment and observation for four weeks, there is no toxicosis reaction yet; and in the reproduction test, the mouse was fed with routine dosages from 7 mg/kg for 3 generations, and it has been proved that the compound of formula (I) has no influence on the pregnancy, birth, nursing and the growth of baby mice. So it is proved that the compound of formula (I) is a substance without toxicity.

III. Observation of Curative Efficiency.

80 patients suffering from motion sickness were selected and randomly divided into four groups: a group to whom N-acetyl-D-glucosamine was administered in a long term (800 mg of NAG/person/day), a group to whom N-acetyl-D-glucosamine was administered in a short term (6000 mg of NAG/person/day), placebo group (6000 mg of glucose/person/day), a group to whom no medicament was administered. A double blind method was adopted, observing the curative efficiency for traveling 100 kilometers by car (its velocity was 20 kilometers/hour) and traveling 100 kilometers by a small steamboat. Compared with the situation before traveling by car, the following symptoms being relieved or removed will be judged to be effective: dizziness, nausea and vomiting. The results can be seen from the following table:

|  | Number of person | Effective | Not effective |
| --- | --- | --- | --- |
| NAG long term group | 20 | 18 | 2 |
| NAG short term group | 20 | 19 | 1 |
| Placebo group | 20 | 3 | 17 |
| No administration | 20 | 2 | 18 |

As shown in the table, the statistic results indicate that the effectivity of preventing and treating motion sickness with N-acetyl-D-glucosamine is more than 90%, remarkably different from the placebo group and the group to which the medicament was not administered ($p<0.05$).

What is claimed is:

1. A method of treating a subject who has been or who will be subjected to movements that can cause motion sickness, the method comprising administering to the subject an effective amount of a medicament comprising N-acetyl-D-glucosamine and/or a pharmaceutically acceptable salt thereof in an amount effective to prevent or to relieve symptoms of motion sickness.

2. The method according to claim 1, wherein said medicament is administrated to the subject orally in form of an oral solution or a solid preparation.

3. The method according to claim 2, wherein said medicament is administered to the subject in an alcoholic drink containing 0.1~4% by weight of N-acetyl-D-glucosamine and/or pharmaceutically acceptable salts thereof.

4. The method according to claim 1, wherein said medicament is administered to the subject in need thereof orally with a dosage of 1,000~10,000 mg of N-acetyl-D-glucosamine and/or a pharmaceutically acceptable salt thereof from 2~3 days before the trip to the end of the trip, wherein the trip is by car, navigation, or flying, for preventing or relieving the symptoms of motion sickness.

5. The method according to claim 1, wherein said medicament is administered to the subject in need thereof orally with a dosage of 200~2,000 mg N-acetyl-D-glucosamine and/or a pharmaceutically acceptable salt thereof daily for preventing or relieving the symptoms of motion sickness for a period exceeding 3 days.

6. The method according to claim 3, wherein said medicament is administrated to the subject in need thereof orally with a dosage of 200~1000 mg of N-acetyl-D-glucosamine and/or pharmaceutically acceptable salts thereof daily from 2~3 days before the trip to the end of the trip, wherein the trip is by car, navigation or flying.

7. The method according to claim 1, wherein the symptoms are selected from the group consisting of dizziness, nausea and vomiting.

8. The method according to claim 7, wherein the medicament is administered to the subject prior to the subject being subjected to movement that can cause motion sickness.

* * * * *